(12) United States Patent
Ellman et al.

(10) Patent No.: US 7,905,882 B1
(45) Date of Patent: Mar. 15, 2011

(54) ACTIVATOR FOR ELECTROSURGICAL HANDPIECE

(76) Inventors: Alan G. Ellman, Oceanside, NY (US); Jon C. Garito, Oceanside, NY (US)

( * ) Notice: Subject to any disclaimer, the term of this patent is extended or adjusted under 35 U.S.C. 154(b) by 985 days.

(21) Appl. No.: 11/799,603

(22) Filed: May 3, 2007

(51) Int. Cl.
*A61B 18/14* (2006.01)
(52) U.S. Cl. ............................ 606/46; 606/41; 600/106
(58) Field of Classification Search .................. 606/41, 606/45–48; 600/104–106, 131
See application file for complete search history.

(56) References Cited

U.S. PATENT DOCUMENTS

| | | | | |
|---|---|---|---|---|
| 4,060,086 A | * | 11/1977 | Storz | 606/46 |
| 5,307,804 A | * | 5/1994 | Bonnet | 600/109 |
| 7,588,569 B2 | * | 9/2009 | Irion et al. | 606/46 |
| 2002/0183743 A1 | * | 12/2002 | Held | 606/46 |
| 2003/0144663 A1 | * | 7/2003 | Berberich et al. | 606/46 |
| 2006/0063975 A1 | * | 3/2006 | Hipp et al. | 600/156 |
| 2010/0063353 A1 | * | 3/2010 | Eliachar et al. | 600/106 |

* cited by examiner

*Primary Examiner* — Michael Peffley

(57) ABSTRACT

A disposable bipolar or unipolar electrosurgical handpiece having an extendable and retractable active electrode end and housed in a relatively inexpensive body comprising an activating handle for use in various electrosurgical procedures. The housing comprises slidable axially-aligned body sections coupled to rigid axially-spaced arms of the actuating handle, the arms extending both below and above the common axis of the body sections and comprising concave portions configured to receive fingers of the user. The arrangement allows the user to use 2, 3 or 4 fingers and thumb to operate the handpiece both in a normal and an inverted position.

8 Claims, 3 Drawing Sheets

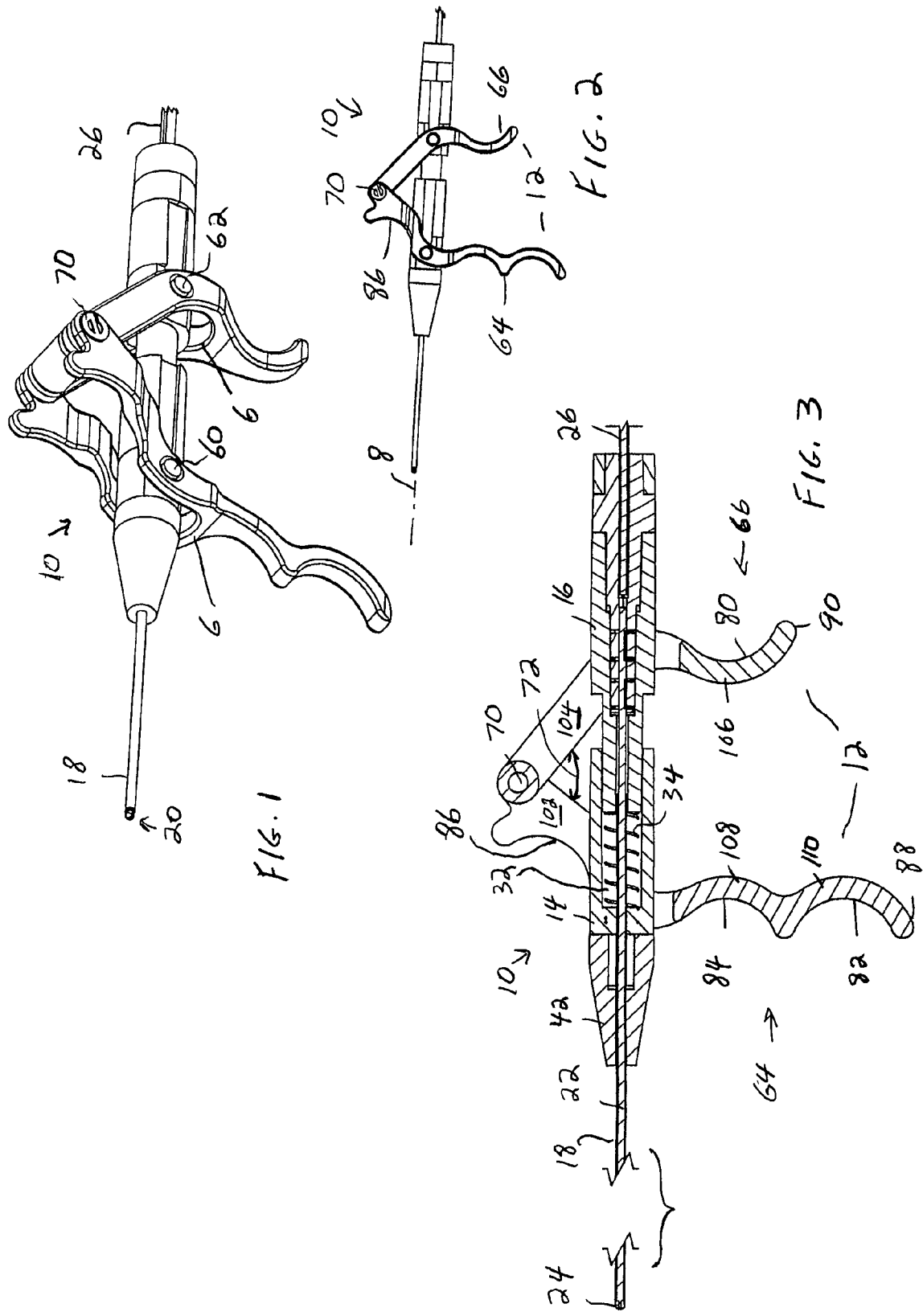

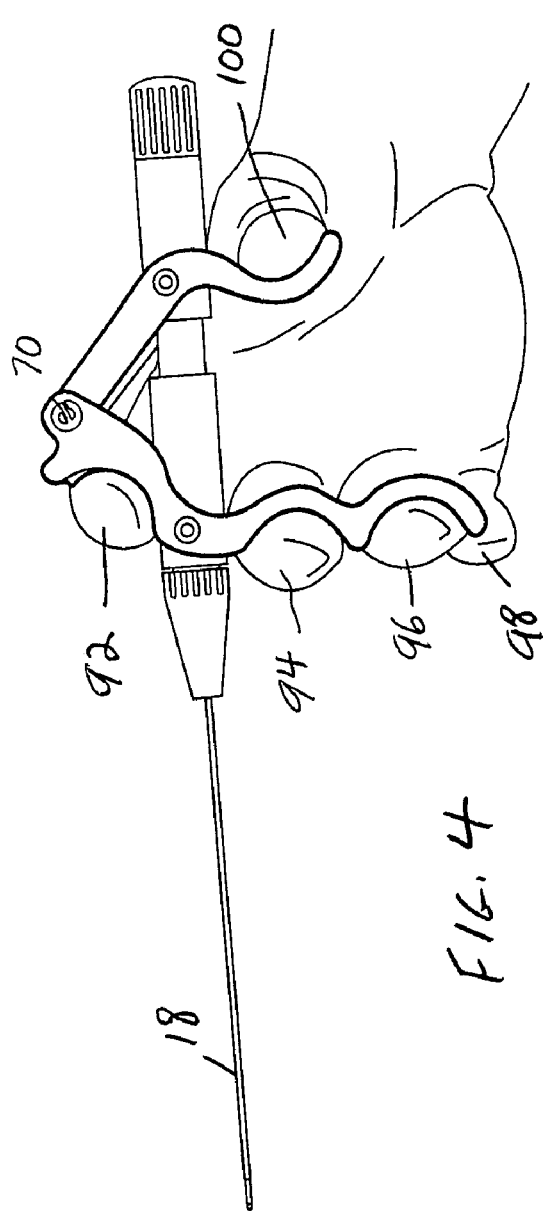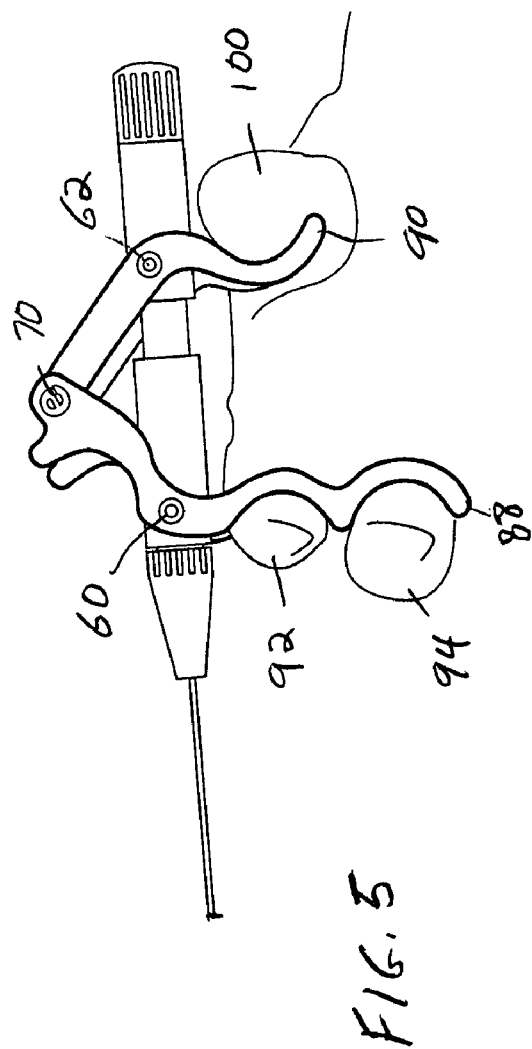

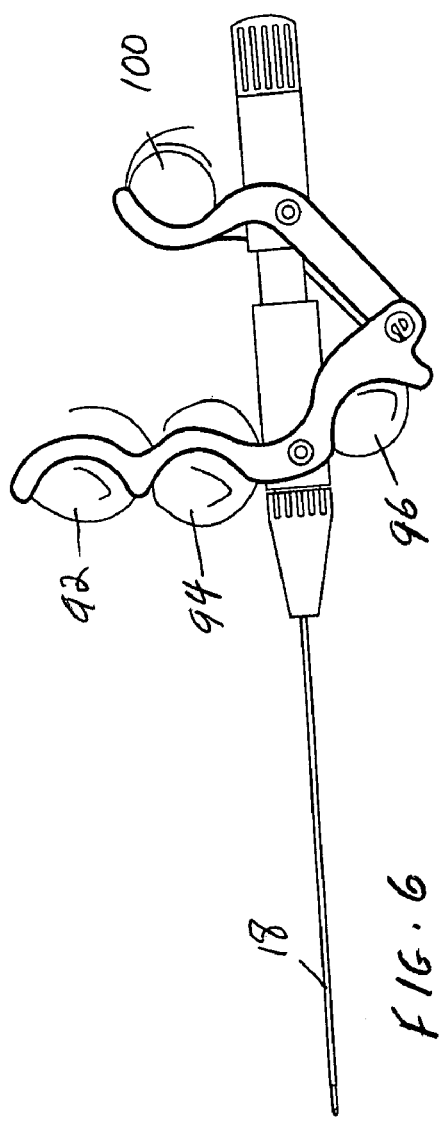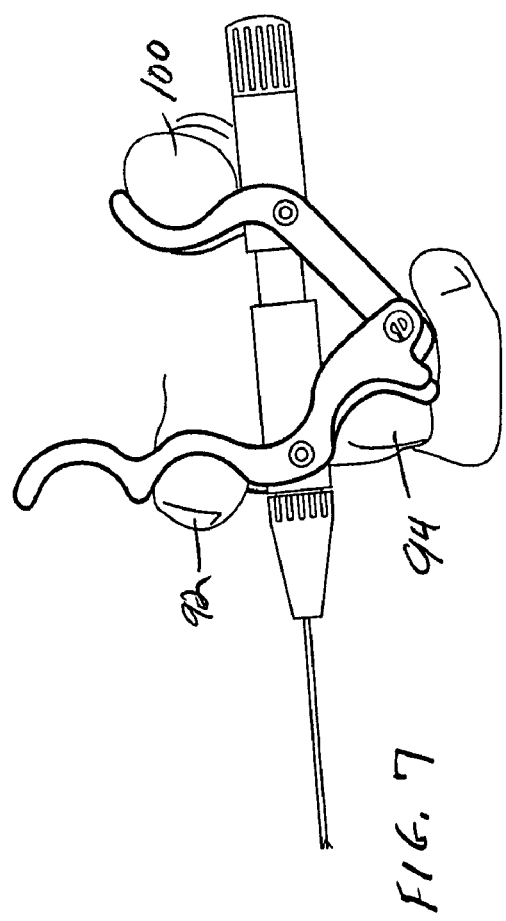
FIG. 6
FIG. 7

ACTIVATOR FOR ELECTROSURGICAL HANDPIECE

This invention relates to an electrosurgical handpiece and an activator for an electrosurgical handpiece.

BACKGROUND OF THE INVENTION

Our prior U.S. Pat. No. 7,101,370, the contents of which are herein incorporated by reference, describes a novel electrosurgical handpiece for treating tissue in a surgical procedure commonly known as minimally invasive surgery (MIS), and is preferably constructed with a flexible tip or end controllable by the surgeon so as to allow the surgeon to manipulate the end as desired during the surgical procedure. It describes a relatively inexpensive handpiece construction for such instruments with flexible tips comprising a first main body, a second main body slidingly coupled to the first main body, a squeezable handle connected to and across the first and second main bodies such that, when the handle is unsqueezed, the first and second main bodies assume a first position relative to one another, and when the handle is squeezed, the first and second main bodies assume a second position relative to one another, spring means for biasing the first and second main bodies into their first position, an elongated tubular first member having a first end and a distal second end, an active electrosurgical electrode slidingly mounted within the tubular first member and extendable from the distal second end of the tubular first member and connected to one of the first and second main bodies, the electrosurgical electrode having a contact end and at least one electrically active end adjacent the distal second end of the tubular first member, and electrical terminal means at one of the first and second main bodies and electrically connected to the electrically active end of the electrosurgical electrode, whereby, when the electrical terminal means is activated and the handle squeezed, the first and second main bodies assume their second position and the electrically active end of the electrode is extended out of the distal second end of the tubular first member and is capable of supplying electrosurgical currents when applied to a patient.

SUMMARY OF THE INVENTION

The new handpiece constructions of the present improvement are focused at the gun or handle end of the handpiece, meaning the part of the handpiece held in the hand of the surgeon and operable by the surgeon to extend and retract the flexible tip. The internal construction of the handpiece employing the new activator can be the same as that described in detail in the referenced patent.

In accordance with a preferred embodiment, the handle activator comprises two axially spaced rigid members pivoted on and extending below the handpiece body, the two members also extending above the handpiece body and joining as levers at a fulcrum.

Preferably, the rigid members are pivoted at midpoints each on one of two relatively movable bodies of the handpiece, their relative position determining the position of the active part of an electrosurgical electrode. In the embodiment described in the referenced patent, the relative position of the movable bodies extends and retracts the active end of the electrode. Also, in this embodiment, the movable bodies are axially spaced and aligned, with one connected to a fixed part of the handpiece and the other connected to the extendable electrode of the handpiece. The invention however is not limited to such arrangements. The bodies while preferably axially aligned need not be axially-spaced, but can also be coaxial. Also, the action obtained when the bodies are moved need not be limited to extension and retraction of an electrode, but can also involve changing the position of an already extended electrode or modifying the position of parts of an extended electrode, such as opening the jaws of an electrode.

In a further preferred embodiment, the handle portions located below their pivot connections to the handpiece body have concave-shaped portions to receive the fingers and thumb of the user as desired, and the handle portion positioned above its pivot connection to the handpiece body also has a concave-shaped portion to receive a finger of the user. The concave portions designed for the user's fingers face forward, whereas the concave portion designed for the user's thumb faces backward.

In a preferred embodiment, the handle or activator of the handpiece is constructed preferably of known plastics, and thus can be, for example, molded in several parts and simply assembled by being force-fitted and/or adhered together by suitable adhesives, or snapped together as is well known in the art for assembling plastic members. Preferably, all parts of the handle end except for electrical terminals, optionally a metal spring, and the electrode assembly are made of inexpensive plastic.

The construction of the invention will provide a low-cost handpiece that can be made disposable with the same important benefits not only for MIS of herniated disks but also for other MIS procedures where controlled electrode position and/or controlled heat generation is of importance as described in the prior applications, as well as for general electrosurgical procedures where the volumetric reduction of tissue is desirable, and in addition provides much greater control by the user over the position of the electrode tip when extended or whose position is modified. It offers the additional advantage of requiring much less effort by the user to modify the position of the active end of the electrode.

While the invention of the handpiece of the invention has focused on low-cost fabrication allowing disposability or one-time use, it will be understood by those skilled in this art that the same handpiece can also be reusable if the practitioner so desires, by appropriate sterilization after each use. Most forms of sterilization can be used by an appropriate choice of handpiece materials, such as high-temperature plastics, but gas sterilization as is well known in this art can also be used if heat-sensitive material may be present.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention, like reference numerals designating the same or similarly functioning parts.

BRIEF DESCRIPTION OF THE DRAWINGS

In the drawings:

FIG. 1 is a perspective view of one form of electrosurgical handpiece in accordance with the invention with the working end shown in its retracted position;

FIG. 2 is a side view of the electrosurgical handpiece of FIG. 1;

FIG. 3 is a vertical cross-sectional view of the electrosurgical handpiece of FIG. 1;

FIGS. 4 and 5 are side views of the electrosurgical handpiece of FIG. 1 showing two different hand positions of the user on the handle;

FIGS. 6 and 7 are side views of the electrosurgical handpiece of FIG. 1 in an inverted position showing two different hand positions of the user on the handle.

DETAILED DESCRIPTION OF THE PREFERRED EMBODIMENTS

The reader is directed to the referenced prior patent for a more detailed description of a flexible tip handpiece which will assist in understanding the improvements offered by the present application. Since the present application otherwise makes use of the same teachings of the prior patent, it was felt unnecessary to repeat in the body of this specification many of the details present in the contents of the prior patents. The present description will be confined solely to the modifications in the handpiece construction that allow for increased control by the user over the extendable tip. In addition, the construction of the present invention can provide both bipolar and unipolar operation separately or in the same handpiece, and can use the same constructions described in the prior patent for providing the extendable and retractable straight and/or curved active electrode tips, as well as many of the details for providing a flexible end or a straight end with a curved extendable electrode, including use in the various medical procedures described in the prior patent and known to others in this art in which electrosurgical currents are used to modulate patient tissue, meaning to cut, ablate, shrink, and/or coagulate tissue.

In the present application, the internal electrode configuration remains essentially the same. It can comprise the use of a pulling wire to flex a flexible end of an outer tube housing for the electrode while simultaneously extending the electrode from the end of the outer tube. Or, preferably, the outer tube end is not flexible, but the electrode distal end is constituted of memory metal or has been given a pre-bent contour such that, when extended from its outer tube housing, it assumes a preset curved or straight position that allows the surgeon to reach with the active end of the electrode patient sites behind, say, other tissues more easily. Other electrode constructions that allow the surgeon to extend an active electrode end from an elongated tubular member and/or cause the active electrode end to assume straight or curved or open configurations are also considered within the scope of the present invention.

FIGS. 1 and 2 show one form of electrosurgical handpiece 10 of the invention, and FIG. 3 shows a cross-sectional view. It will be observed that the cross-sectional view of the handpiece interior is identical to that of FIG. 2 of the referenced patent. It comprises a squeezable handle 12 assembly connected to and across two front 14 and rear 16 main slideable coaxially-aligned body parts enclosing an elongated outer tubular housing 18 from whose distal end 20 an inner electrode 22 with adjacent active bipolar tips 24 can be extended and retracted when the handle 12 is squeezed or released, respectively. The handpiece common axis is designated 8 in FIG. 2. At the right end an electrical cord 26 is terminated in a plug connector (not shown). Internally of the handpiece, wires of the electrical cord 26 are connected to the active electrode 22. The outer tubular housing 18 extends from the front at the left completely through the center of the front body part 14 and into the coaxially-aligned rear body part 16 and terminates in the latter. The front body part 14 contains a bore 32 which houses a compression spring 34 engaged by a reduced diameter projecting member of the rear body part 16.

The compression spring 34 biases apart the two body parts 14, 16. The handle 12 keeps the body parts 14, 16 from relatively axially rotating. The front body part 14 also has a forwardly-projecting cylindrical collet containing several longitudinal slits (not shown). Onto the forwardly-projecting collet is mounted a nose piece 42 with an internal tapered bore (not shown) which is configured to cooperate in the conventional manner with the collet so that when the nose piece is forced onto the forwardly-projecting collet, the collet part closes along the slits and locks to the outer tubular housing 18. In the embodiment shown, the nose piece 42 is permanently secured to the collet 38 so that the electrode is not changeable. The electrical connecting arrangement described and illustrated in FIGS. 6 and 7 of the patent is preferred because it allows for easy interconnections and assembly of the handpiece, without the need for welding or soldering operations.

The assembly can be made permanent by force-fitting together of the parts or by using adhesives between the assembled parts. A preferred way is to slightly taper the various parts that telescope together, apply as by brushing to the eternal surface of the inner fitting part a suitable solvent for the plastic, and force the parts together. The solvent slightly dissolves a thin surface layer of the plastic and when the solvent evaporates, the two contacted parts are essentially fused together permanently. To complete the assembly, after the two sections have been individually assembled, the spring 34 is inserted, and the projecting part assembled to the bore 32, the spring is then compressed, and the handle 12 mounted across the two body parts. The mounting of the handle assembly 12 to the elongated handpiece 10 is the same as is used with the handpiece of the referenced patent. In particular, the front body section 14 is provided with a pivot pin 60 at the axis 8 which is securely attached to that section 14. Similarly, the rear body section 16 is provided with a pivot pin 62 at the axis 8 which is securely attached to that rear section 16. The handle assembly comprises a front handle part 64 and a rear handle part 66 axially spaced from the former, both of which extend below the axis 8 of the handpiece when the latter is held in its upright position as illustrated in FIG. 2. The upper end of each handle part is bifurcated 6 just below its respective pivot point 60, 62, and then the bifurcated handle parts extend upward above the axis 8 and are angled toward one another and joined at a fulcrum point 70. Actually, the latter is an axis due to the bifurcated upper section. The joined handle parts define an inner acute angle 72. The pivotable mounting of the handle parts on their respective pivot pins are freely rotatable, and their junction at the fulcrum point 70 is also freely rotatable. Each of the handle parts 64, 66 are rigid members.

The handle assembly of the invention 12 is configured so that the user can use different fingers of one hand to squeeze the two handle parts, with fingers on both sides of the handpiece handle, and with the handpiece upright or inverted or upside down. This is possible because of the novel concave-shaped regions provided on the handle parts. Specifically, four concave-shaped sections are provided, one 80 on the rear handle part facing rearward, two 82, 84 on the bottom side of the front handle part facing frontward, and one 86 on the top side of the front handle part also facing frontward. Each of the front and rear handle parts, designated generally 64 and 66, are rigid members from their lowest points, designated 88, 90, to where they join at the fulcrum axis 70.

FIGS. 4-7 show the different positions in which a user can hold the handpiece while performing a procedure. In comparison with the referenced patent, which is a whole hand articulating device, the construction of the invention is meant for 4, 3, or 2-finger control. Using just fingertips to articulate the handle allows for finer feedback, as there is a higher nerve density at fingertips as opposed to the middle or base of fingers. Using the first 2 fingers (pointer 92 and middle finger 94) gives the most control, and using the last 2 fingers (index 96 and pinky 98 fingers) gives the least control. The thumb, treated herein as a finger, is designated 100. FIG. 4 shows the use of 4 fingers, 92, 94, 96, 100, positioned in all four arc-shaped regions. FIG. 5 shows the use of 3 fingers, 92, 94, 100, the arc-shaped region at the top being omitted. The operation can also be reduced to the use of 2 fingers, the pointer 94 or middle finger 96, and the thumb 100. FIGS. 6 and 7 show, respectively, the use of 4 fingers, 92, 94, 96, 100, and 3 fingers, 92, 94, 100, while holding the handpiece in an inverted position. Used upside down or sideways where space limitations are imposed provides no reduction in performance or ergonomics.

The combination of the pivot points 60, 62 and the fulcrum point 70, for the dimensions shown in the drawings, provides the user with an approximate mechanical advantage of 2:1, which depends on the distance of the fulcrum 70 to each of the pivot points 60, 62 as well as to the bottom ends 88, 90 of the handle members as illustrated in FIG. 2. For the illustrated embodiment, wherein the angle 72 is about 80° and the length of the upper arm portions 102, 104 from the fulcrum 70 to the pivots 60, 62 is about 1.5 inches, the length of the rear lower arm portion 106 from the pivot 62 to its lower end point 90 is about 1.5 inches, the length of the front lower arm portion 108 from the pivot 60 to its midpoint is about 1.5 inches, and the length of the rear lower arm portion 106 from its midpoint to its lower end point 88 is also about 1.5 inches, the mechanical advantage is about 2:1. The mechanical advantage can be reduced or increased by adjusting the lengths of the arm portions that make up the handle. For example, the angle 72 can be varied from about 60-100°. The respective lengths of the various arm members can be varied from about 1 inch to about 2 inches. The shorter the arm lengths, the more convenient the instrument is to use, but the mechanical advantage is reduced. Similarly, the longer the arm lengths, the less convenient the instrument is to use, but the mechanical advantage is increased. It will be appreciated that, in the absence of the fulcrum attachment (it should be understood that point 70 is designated as the fulcrum to distinguish it from the two pivot points 60, 62), since each handle part 64, 66 as a rigid member is pivoted at an approximate midpoint on a pivot pin 60, 62 of each of the front and rear body sections 14, 16, respectively, each will freely rotate about its respective pivot point. The pivot points 60, 62 incidentally are in the same plane as the handpiece axis 8 or centerline. Similarly, the two handle parts 64, 66 each rotate freely where they join about the fulcrum 70. It is this unique arrangement that provides the increased control of the electrode tip when extended, which not only makes the device easier to squeeze, but also de-magnifies the user input for finer position control of the electrode tip. In general, the movement of the handle parts is proportionally larger then the corresponding movement of the electrode tip. Modifications are also possible with varying degrees of de-magnification by altering the locations of the concave finger rests and fulcrum point relative to the pivot points. Another way of understanding the mechanism is to note the value of the inside acute angle, designated 72, formed by the two handle parts where they meet at the fulcrum. As the handle is squeezed, that inside angle 72 decreases, with the result that the corresponding amount of electrode tip extension also gradually reduces as the axial distance between the handle parts 64, 66 reduces.

The new handle configuration also reduces the overall height of the instrument which allows more freedom when in tight positions, especially noticeable when the instrument is close to the user's body.

Since the novel handle design is completely external to the handpiece device, other versions can readily be made without changing the base parts. During the assembly, the handle parts 64, 66 snap onto the associated pivot point 60, 62 molded into the two handpiece sections 14, 16. The fulcrum, essentially an axis about which the two handle parts can rotate, is made when the front and rear sections of the handle are snapped together.

None of the figures show the handpiece with its handles squeezed together and the electrode tip extended, as this action is identical with that shown in FIG. 3 of the referenced patent. It is again noted that the action when the activator is squeezed does not necessarily require electrode extension, but can also involve simply modifying the electrode position if extended, or modifying an electrode part such as to open an electrode jaw.

As used herein, by "axial" is meant parallel to the long axis of the handpiece and electrode (horizontal in FIG. 2). By "lateral" is meant transverse to the long axis.

Once the surgeon has positioned the working end of the handpiece with respect to the tissue to be operated on, he or she then activates the electrosurgical apparatus causing a discharge of bipolar currents between the bare electrode loop ends 24 capable of causing ablation, shrinkage, or excision of tissue, or cauterization of a blood vessel in the usual way. Other usable mechanical or electrical structures following the teachings of the prior patents will be appreciated by those skilled in this art. As with the embodiments of the prior patents, the insulating tube 18 will prevent accidental touching of patient tissue by the electrode sides, so that the bipolar discharge is localized to the spacing between the bare ends.

In all embodiments, the tubular housing 18 can be plastic, such as ABS or DELRIN, or of insulated relatively stiff metal that will not bend.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical handpiece comprising:
    (a) a first main body,
    (b) a second main body axially aligned with and coupled to the first main body,
    (c) a squeezable handle connected to the first and second main bodies such that, when the handle is unsqueezed, the first and second main bodies assume a first axial position relative to one another, and when the handle is squeezed, the first and second main bodies assume a second axial position relative to one another,
    (d) means for biasing the first and second main bodies into their first position,
    (e) a first member having a first end and a second end and connected to one of the first and second main bodies,
    (f) an active electrosurgical electrode connected to the first member and movable into an active position at the second end of the first member and connected to the other of the first and second main bodies, the electrosurgical electrode having a contact end and at least one electrically active end adjacent the second end of the first member, (g) electrical terminal means at one of the first and second main bodies and electrically connected to the electrically active end of the electrosurgical electrode, whereby, when the electrical terminal means is activated and the handle squeezed, the first and second main bodies assume their second position and the electrically active end of the electrode can be moved into its active position at the second end of the first member and is capable of supplying electrosurgical currents when applied to a patient, characterized in that:

the squeezable handle comprises:

(h) a first rigid arm member pivotably connected at a midpoint to the first main body and having a first arm portion extending below its pivotably-connected midpoint and a second arm portion extending above its pivotably-connected midpoint, (i) a second rigid arm member pivotably connected at a midpoint to the second main body and having a first arm portion extending below its pivotably-connected midpoint and a second arm portion extending above its pivotably-connected midpoint, (j) the second arm portions of the first and second arm members being joined together above their pivotably-connected midpoints to form a pivotable fulcrum axis.

2. An electrosurgical handpiece as claimed in claim 1, wherein the second arm portions of the first and second arm members form at the fulcrum an angle of about 60-100°.

3. An electrosurgical handpiece as claimed in claim 1, wherein the first and second arm portions are dimensioned to provide a mechanical advantage of about 2:1 for the user.

4. An electrosurgical handpiece comprising:

(a) a first main body, (b) a second main body axially aligned with and rearwardly of and slidingly coupled to the first main body, (c) a squeezable handle connected to and across the first and second main bodies such that, when the handle is unsqueezed, the first and second main bodies assume a first axial position relative to one another, and when the handle is squeezed, the first and second main bodies assume a second axial position relative to one another, (d) spring means for biasing the first and second main bodies into their first position, (e) an elongated tubular first member having a first end and a distal second end and connected to one of the first and second bodies, (f) an active electrosurgical electrode slidingly mounted within the tubular first member and extendable from the distal second end of the tubular first member and connected to the other of the first and second main bodies, the electrosurgical electrode having a contact end and at least one electrically active end adjacent the distal second end of the tubular first member, (g) electrical terminal means at one of the first and second main bodies and electrically connected to the electrically active end of the electrosurgical electrode, whereby, when the electrical terminal means is activated and the handle squeezed, the first and second main bodies assume their second position and the electrically active end of the electrode can be extended out of the distal second end of the tubular first member and is capable of supplying electrosurgical currents when applied to a patient, characterized in that:

the squeezable handle comprises:

(h) a first rigid arm member pivotably connected at a midpoint to the first main body and having a first arm portion extending below its pivotably-connected midpoint and a second arm portion extending above its pivotably-connected midpoint, (i) a second rigid arm member pivotably connected at a midpoint to the second main body and having a first arm portion extending below and a second arm portion extending above its pivotably-connected midpoint, (j) the second arm portions of the first and second arm members being joined together above their pivotably-connected midpoints to form a pivotable fulcrum axis.

5. An electrosurgical handpiece as claimed in claim 4, wherein the first arm portion of the first arm member comprises a first finger-receiving concave portion facing in the direction of the distal second end of the tubular first member, the first arm portion of the second arm member comprises a second finger-receiving concave portion facing in the direction of the first end of the tubular first member.

6. An electrosurgical handpiece as claimed in claim 5, wherein the first arm portion of the first arm member comprises a third finger-receiving concave portion extending below the first concave portion and also facing in the direction of the distal second end of the tubular first member.

7. An electrosurgical handpiece as claimed in claim 6, wherein the second arm portion of the first arm member comprises a fourth finger-receiving concave portion facing in the direction of the distal second end of the tubular first member.

8. An electrosurgical handpiece as claimed in claim 7, wherein the first, second, third, and fourth concave portions of the handle are configured to receive fingers of a user.

\* \* \* \* \*